(12) United States Patent
Lauffer et al.

(10) Patent No.: US 7,253,264 B1
(45) Date of Patent: Aug. 7, 2007

(54) IMMUNOGLOBULIN FUSION PROTEINS, THEIR PRODUCTION AND USE

(75) Inventors: Leander Lauffer, Marbury (DE); Gerd Zettlmeissl, Wetter (DE); Patricia Oquendo, Marburg (DE); Brian Seed, Boston, MA (US)

(73) Assignees: Sanofi-Arentideutschland GmbH (DE); The General Hospital Corporation, Boston, MA (US)

( * ) Notice: Subject to any disclaimer, the term of this patent is extended or adjusted under 35 U.S.C. 154(b) by 0 days.

(21) Appl. No.: 08/293,603

(22) Filed: Aug. 22, 1994

Related U.S. Application Data

(63) Continuation of application No. 08/013,229, filed on Feb. 1, 1993, now abandoned, which is a continuation of application No. 07/581,703, filed on Sep. 13, 1990, now abandoned.

(30) Foreign Application Priority Data

Jun. 28, 1990 (DE) .................................. 40 20 607

(51) Int. Cl.
*C07K 19/00* (2006.01)
(52) U.S. Cl. .............. 530/387.9; 435/69.7; 530/388.23
(58) Field of Classification Search ................ 530/387, 530/350, 395; 536/27, 23.4, 23.5, 23.53; 435/69.7; 424/198.1
See application file for complete search history.

(56) References Cited

U.S. PATENT DOCUMENTS

| 4,816,567 A | 3/1989 | Cabilly et al. .............. 530/387 |
|---|---|---|
| 5,264,416 A | 11/1993 | Park et al. ...................... 514/2 |
| 5,395,760 A | 3/1995 | Smith et al. ................ 435/365 |
| 5,428,130 A | 6/1995 | Capon et al. ............... 530/350 |
| 5,455,165 A | 10/1995 | Capon et al. .............. 435/69.7 |
| 5,512,544 A | 4/1996 | Wallach et al. ............... 514/12 |
| 5,599,905 A | 2/1997 | Mosley et al. ............. 530/350 |
| 5,605,690 A | 2/1997 | Jacobs et al. ............ 424/134.1 |
| 5,610,279 A | 3/1997 | Brockhaus et al. ....... 530/387.3 |
| 5,712,155 A | 1/1998 | Smith et al. ............ 435/320.1 |

FOREIGN PATENT DOCUMENTS

| EP | 0 269 455 | 6/1988 |
|---|---|---|
| EP | 0 325 262 | 7/1989 |
| EP | 0 414 178 | 2/1991 |

OTHER PUBLICATIONS

Strader et al. FASEB J. 3, 1825-1832, 1989.*
European Search Report for EP 97 12 0664, mailed Mar. 9, 1998.

* cited by examiner

*Primary Examiner*—LM Spector
(74) *Attorney, Agent, or Firm*—Clark & Elbing LLP

(57) ABSTRACT

The invention relates to genetically engineered soluble fusion proteins composed of human proteins not belonging to the immunoglobulin family, or of parts thereof, and of various portions of the constant region of immunoglobulin molecules. The functional properties of the two fusion partners are surprisingly retained in the fusion protein.

6 Claims, 11 Drawing Sheets

```
    GTCGCTCGGACGCTCCTGCTCGGCTGGGTCTTCGCCCAGGTGGCCGGCGCTTCAGGCACT
121 ---------+---------+---------+---------+---------+---------+ 180
    CAGCGAGCCTGCGAGGACGAGCCGACCCAGAAGCGGGTCCACCGGCCGCGAAGTCCGTGA
                                 <**************************
                                 oligonucleotide ACAAATACTGTGGCAGCATATAATTTAACTTGGAAATCAACTAATTTCAAGACAATTTTG
181 ---------+---------+---------+---------+---------+---------+ 240
    TGTTTATGACACCGTCGTATATTAAATTGAACCTTTAGTTGATTAAAGTTCTGTTAAAAC
    **************************|

======================================================================== oligonucleotide
    |***********************************************>
    AACTACTGTTTCAGTGTTCAAGCAGTGATTCCCTCCCGAACAGTTAACCGGAAGAGTACA
721 ---------+---------+---------+---------+---------+---------+ 780
    TTGATGACAAAGTCACAAGTTCGTCACTAAGGGAGGGCTTGTCAATTGGCCTTCTCATGT
```

Fig. 1

```
              10                  30                  50
GCCCCCCCTCGAGGTCGACGGTATCGATAAGCTTGATATCGAATTCTCTCGGCGAACCCC 70                  90                 110
CTCGCACTCCCTCTGGCCGGCCCAGGGCGCCTTCAGCCCAACCTCCCCAGCCCCACGGGC 130                 150                 170
GCCACGGAACCCGCTCGATCTCGCCGCCAACTGGTAGACATGGAGACCCCTGCCTGGCCC
                                        MetGluThrProAlaTrpPro 190                 210                 230
CGGGTCCCGCGCCCCGAGACCGCCGTCGCTCGGACGCTCCTGCTCGGCTGGGTCTTCGCC
ArgValProArgProGluThrAlaValAlaArgThrLeuLeuLeuGlyTrpValPheAla 250                 270                 290
CAGGTGGCCGGCGCTTCAGGCACTACAAATACTGTGGCAGCATATAATTTAACTTGGAAA
GlnValAlaGlyAlaSerGlyThrThrAsnThrValAlaAlaTyrAsnLeuThrTrpLys 310                 330                 350
TCAACTAATTTCAAGACAATTTTGGAGTGGGAACCCAAACCCGTCAATCAAGTCTACACT
SerThrAsnPheLysThrIleLeuGluTrpGluProLysProValAsnGlnValTyrThr 370                 390                 410
GTTCAAATAAGCACTAAGTCAGGAGATTGGAAAAGCAAATGCTTTTACACAACAGACACA
ValGlnIleSerThrLysSerGlyAspTrpLysSerLysCysPheTyrThrThrAspThr 430                 450                 470
GAGTGTGACCTCACCGACGAGATTGTGAAGGATGTGAAGCAGACGTACTTGGCACGGGTC
GluCysAspLeuThrAspGluIleValLysAspValLysGlnThrTyrLeuAlaArgVal 490                 510                 530
TTCTCCTACCCGGCAGGGAATGTGGAGAGCACCGGTTCTGCTGGGGAGCCTCTGTATGAG
PheSerTyrProAlaGlyAsnValGluSerThrGlySerAlaGlyGluProLeuTyrGlu 550                 570                 590
AACTCCCCAGAGTTCACACCTTACCTGGAGACAAACCTCGGACAGCCAACAATTCAGAGT
AsnSerProGluPheThrProTyrLeuGluThrAsnLeuGlyGlnProThrIleGlnSer
```

Fig. 2

```
        610                 630                 650
TTTGAACAGGTGGGAACAAAAGTGAATGTGACCGTAGAAGATGAACGGACTTTAGTCAGA
PheGluGlnValGlyThrLysValAsnValThrValGluAspGluArgThrLeuValArg 670                 690                 710
AGGAACAACACTTTCCTAAGCCTCCGGGATGTTTTTGGCAAGGACTTAATTTATACACTT
ArgAsnAsnThrPheLeuSerLeuArgAspValPheGlyLysAspLeuIleTyrThrLeu 730                 750                 770
TATTATTGGAAATCTTCAAGTTCAGGAAAGAAAACAGCCAAAACAAACACTAATGAGTTT
TyrTyrTrpLysSerSerSerSerGlyLysLysThrAlaLysThrAsnThrAsnGluPhe 790                 810                 830
TTGATTGATGTGGATAAAGGAGAAAACTACTGTTTCAGTGTTCAAGCAGTGATTCCCTCC
LeuIleAspValAspLysGlyGluAsnTyrCysPheSerValGlnAlaValIleProSer 850                 870                 890
CGAACAGTTAACCGGAAGAGTACAGACAGCCCGGTAGAGTGTATGGGCCAGGAGAAAGGG
ArgThrValAsnArgLysSerThrAspSerProValGluCysMetGlyGlnGluLysGly 910                 930                 950
GAATTCAGAGAAATATTCTACATCATTGGAGCTGTGGTATTTGTGGTCATCATCCTTGTC
GluPheArgGluIlePheTyrIleIleGlyAlaValValPheValValIleIleLeuVal 970                 990                1010
ATCATCCTGGCTATATCTCTACACAAGTGTAGAAAGGCAGGAGTGGGGCAGAGCTGGAAG
IleIleLeuAlaIleSerLeuHisLysCysArgLysAlaGlyValGlyGlnSerTrpLys 1030                1050                1070
GAGAACTCCCCACTGAATGTTTCATAAAGGAAGCACTGTTGGAGCTACTGCAAATGCTAT
GluAsnSerProLeuAsnValSer 1090                1110                1130
ATTGCACTGTGACCGAGAACTTTTAAGAGGATAGAATACATGGAAACGCAAATGAGTATT 1150                1170                1190
TCGGAGCATGAAGACCCTGGAGTTCAAAAAACTCTTGATATGACCTGTTATTACCATTAG
```

Fig. 2
(continued)

```
         1210                1230                1250
CATTCTGGTTTTGACATCAGCATTAGTCACTTTGAAATGTAACGAATGGTACTACAACCA 1270                1290                1310
ATTCCAAGTTTTAATTTTTAACACCATGGCACCTTTTGCACATAACATGCTTTAGATTAT 1330                1350                1370
ATATTCCGCACTTAAGGATTAACCAGGTCGTCCAAGCAAAAACAAATGGGAAAATGTCTT 1390                1410                1430
AAAAAATCCTGGGTGGACTTTTGAAAAGCTTTTTTTTTTTTTTTTTGAGACGGAGTC 1450                1470                1490
TTGCTCTGTTGCCCAGGCTGGAGTGCAGTAGCACGATCTCGGCTCACTTGCACCCTCCGT 1510                1530                1550
CTCTCGGGTTCAAGCAATTGTCTGCCTCAGCCTCCCGAGTAGCTGGGATTACAGGTGCGC 1570                1590                1610
ACTACCACGCCAAGCTAATTTTTGTATTTTTTAGTAGAGATGGGGTTTCACCATCTTGGC 1630                1650                1670
CAGGCTGGTCTTGAATTCCTGACCTCAGTGATCCACCCACCTTGGCCTCCCAAAGATGCT 1690                1710                1730
AGTATTATGGGCGTGAACCACCATGCCCAGCCGAAAAGCTTTTGAGGGGCTGACTTCAAT 1750                1770                1790
CCATGTAGGAAAGTAAAATGGAAGGAAATTGGGTGCATTTCTAGGACTTTTCTAACATAT 1810                1830                1850
GTCTATAATATAGTGTTTAGGTTCTTTTTTTTTCAGGAATACATTTGGAAATTCAAAAC 1870                1890                1910
AATTGGGCAAACTTTGTATTAATGTGTTAAGTGCAGGAGACATTGGTATTCTGGGCAGCT
```

Fig. 2
(continued)

```
        1930                1950                1970
TCCTAATATGCTTTACAATCTGCACTTTAACTGACTTAAGTGGCATTAAACATTTGAGAG 1990                2010                2030
CTAACTATATTTTTATAAGACTACTATACAAACTACAGAGTTTATGATTTAAGGTACTTA 2050                2070                2090
AAGCTTCTATGGTTGACATTGTATATATAATTTTTTAAAAAGGTTTTTCTATATGGGGAT 2110                2130                2150
TTTCTATTTATGTAGGTAATATTGTTCTATTTGTATATATTGAGATAATTTATTTAATAT

2170
ACTTTAAATAAAGGTGACTGGGAATTGTT
```

Fig. 2
(continued)

```
                    HindIII
       5' GATCGATTAAGCTTCGGAACCCGCTCGATCTCGCCGCC 3' Oligonucleotide A
                 ------||||||||||||||||||||||||||||
          AGCCCCACGGGCGCCACGGAACCCGCTCGATCTCGCCGCCAACTGGTAGACATGGAG
  110   ---------+---------+---------+---------+---------+------- 167
          TCGGGGTGCCCGCGGTGCCTTGGGCGAGCTAGAGCGGCGGTTGACCATCTGTACCTC MetGlu
       -------------------------------------------------|------
                                  5'-non-translated      Start
                                                         Reading frame
                                                         (signal peptide)

==========================================================================

End extracellular domain  |  Start transmembrane region
       -----------------------|-----------------------
       GlnGluLysGlyGluPheArgGluIlePheTyrIleIleGlyAlaVal
       CAGGAGAAAGGGGAATTCAGAGAAATATTCTACATCATTGGAGCTGTGGT
  890  ---------+---------+---------+---------+---------+ 940
       GTCCTCTTTCCCCTTAAGTCTCTTTATAAGATGTAGTAACCTCGACACCA
                 |||||||||||||||||||||||||||||
            3' CCCCTTAAGTCTCTTTATAAGATGCCCCTAGGTCTATACG 5' Oligonucleotide B
                                                ------
                                                BamHI
```

Fig. 3

```
                XhoI
5' GATCCAGTACTCGAGAGAGAAGCCGGGCGTGGTGGCTCATGC 3'        Oligonucleotide A
         ------||||||||||||||||||||||||||||||
             AGAGAAGCCGGGCGTGGTGGCTCATGCCTATAATCCCAGCACTTTTGGAGGCTGAGGCGG
       61 ---------+---------+---------+---------+---------+---------+ 120
             TCTCTTCGGCCCGCACCACCGAGTACGGATATTAGGGTCGTGAAAACCTCCGACTCCGCC ------------------ 5' -non-translated  ----------------

GCAGATCACTTGAGATCAGGAGTTCGAGACCAGCCTGGTGCCTTGGCATCTCCCAATGGG
      121 ---------+---------+---------+---------+---------+---------+ 180
             CGTCTAGTGAACTCTAGTCCTCAAGCTCTGGTCGGACCACGGAACCGTAGAGGGTTACCC

--------- 5' -non-translated  ---------------------|MetGly

Start
                                                         Reading frame
                                                         (signal peptide)

================================================================================

End extracellular domain  |  Start transmembrane region
             ---------------------------------|--------------------------
             HisAsnSerTyrArgGluProPheGluGlnHisLeuLeuLeuGlyValSerValSerCys
             CACAACTCCTACAGGGAGCCCTTCGAGCAGCACCTCCTGCTGGGCGTCAGCGTTTCCTGC
      839 -+---------+---------+---------+---------+---------+-------- 898
             GTGTTGAGGATGTCCCTCGGGAAGCTCGTCGTGGAGGACGACCCGCAGTCGCAAAGGACG
             ||||||||||||||||||||||||||||||||||
       3' GTGTTGAGGATGTCCCTCGGGAAGCTCGTCCTAGGTACAGTATC 5'    Oligonucleotide B
                                            ------
                                            BamHI
```

Fig. 5

```
                XhoI
5' GATCGATCTCGAGATGGGGGTGCACGAATGTCCTGCCTGGCTGTGG 3' Oligonucleotide A
         ------|||||||||||||||||||||||||||||||||||
               ATGGGGGTGCACGAATGTCCTGCCTGGCTGTGGCTTCTCCTGTCCCTGCTGTCG
      182 --------+---------+---------+---------+---------+----- 235
               TACCCCCACGTGCTTACAGGACGGACCGACACCGAAGAGGACAGGGACGACAGC MetGlyValHisGluCysProAlaTrpLeuTrpLeuLeuLeuSerLeuLeuSer -

Begin reading frame (signal peptide)
```

===========================================================================

```
       End reading frame --------------|
       LeuTyrThrGlyGluAlaCysArgThrGlyAspArgEnd
       --------------------------------------|
       GCTGTACACAGGGGAGGCCTGCAGGACAGGGGACAGATGACCAGGTGTGTCCACCTGGGC
   724 -------+---------+---------+---------+---------+---------+--- 783
       CGACATGTGTCCCCTCCGGACGTCCTGTCCCCTGTCTACTGGTCCACACAGGTGGACCCG
       |||||||||||||||||||||||||||||||||||||
    3' CGACATGTGTCCCCTCCGGACGTCCTGTCCCCTAGGCTAAGGTC 5' Oligonucleotide B
                                         ------
                                         BamHI
```

Fig. 7

IMMUNOGLOBULIN FUSION PROTEINS, THEIR PRODUCTION AND USE

This application is a continuation of U.S. patent application Ser. No. 08/013,229, filed Feb. 1, 1993.

This application is a continuation of U.S. patent application Ser. No. 07/581,703, filed Sep. 13, 1990.

FIELD OF THE INVENTION

The invention relates to genetically engineered soluble fusion proteins composed of human proteins not belonging to the immunoglobulin family, or of parts thereof, and of various portions of the constant region of immunoglobulin molecules. The functional properties of the two fusion partners are, surprisingly, retained in the fusion protein.

BACKGROUND OF THE INVENTION

EP-A 0 325 262 and EP-A 0 314 317 disclose corresponding fusion proteins composed of various domains of the CD4 membrane protein of human T cells and of human IgG1 portions. Some of these fusion proteins bind with the same affinity to the glycoprotein gp120 of human immunodeficiency virus as the cell-bound CD4 molecule. The CD4 molecule belongs to the immunoglobulin family and, consequently, has a very similar tertiary structure to that of immunoglobulin molecules. This also applies to the α chain of the T-cell antigen receptor, for which such fusions have also been described (Gascoigne et al., Proc. Natl. Acad. Sci. USA, vol. 84 (1987), 2937–2940). Hence, on the basis of the very similar domain structure, in this case retention of the biological activity of the two fusion partners in the fusion protein was to be expected.

SUMMARY OF THE INVENTION

The human proteins which are, according to the invention, preferably coupled to the amino terminus of the constant region of immunoglobulin do not belong to the immunoglobulin family and are to be assigned to the following classes: (i) membrane-bound proteins whose extracellular domain is wholly or partly incorporated in the fusion. These are, in particular, thromboplastin and cytokine receptors and growth factor receptors, such as the cellular receptors for interleukin-4, interleukin-7, tumor necrosis factor, GM-CSF, G-CSF, erythropoietin; (ii) non-membrane-bound soluble proteins which are wholly or partly incorporated in the fusion. These are, in particularly, proteins of therapeutic interest such as, for example, erythropoietin and other cytokines and growth factors.

The fusion proteins can be prepared in known pro- and eukaryotic expression systems, but preferably in mammalian cells (for example CHO, COS and BHK cells).

The fusion proteins according to the invention are, by reason of their immunoglobulin portion, easy to purify by affinity chromatography and have improved pharmacokinetic properties in vivo.

The invention thus relates to genetically engineered soluble fusion proteins composed of human proteins not belonging to the immunoglobulin family, or of parts thereof, and of various portions of the constant regions of heavy or light chains of immunoglobulins of various subclasses (IgG, IgM, IgA, IgE). Preferred as immunoglobulin is the constant part of the heavy chain of human IgG, particularly preferably of human IgG1, where fusion takes place at the hinge region.

When fusion takes place at the hinge region, the resulting fusion protein contains the domains of the constant region of a human immunoglobulin heavy chain other than the first domain of said constant region.

Furthermore, the invention relates to processes for the preparation of these fusion proteins by genetic engineering, and to the use thereof for diagnosis and therapy.

BRIEF DESCRIPTION OF THE DRAWINGS

FIG. 1 depicts the sequence of two oligonucleotide probes derived from thromboplastin cDNA.

FIG. 2 depicts the sequence of the clone 2b-Apr5 with thromboplastin amino acid sequence deduced therefrom.

FIG. 3 depicts the sequence homology of oligonucleotide A and oligonucleotide B with the coding and noncoding strands, respectively, with thromboplastin cDNA.

FIG. 5 depicts the sequence homology of oligonucleotide A and oligonucleotide B with the coding and noncoding strands, respectively, with the IL-4 receptor cDNA.

FIG. 7 depicts the sequence homology of oligonucleotide A and oligonucleotide B with the coding and noncoding strands, respectively, with EPO cDNA.

DETAILED DESCRIPTION OF THE PREFERRED EMBODIMENTS AND EXAMPLES

Figure 4:
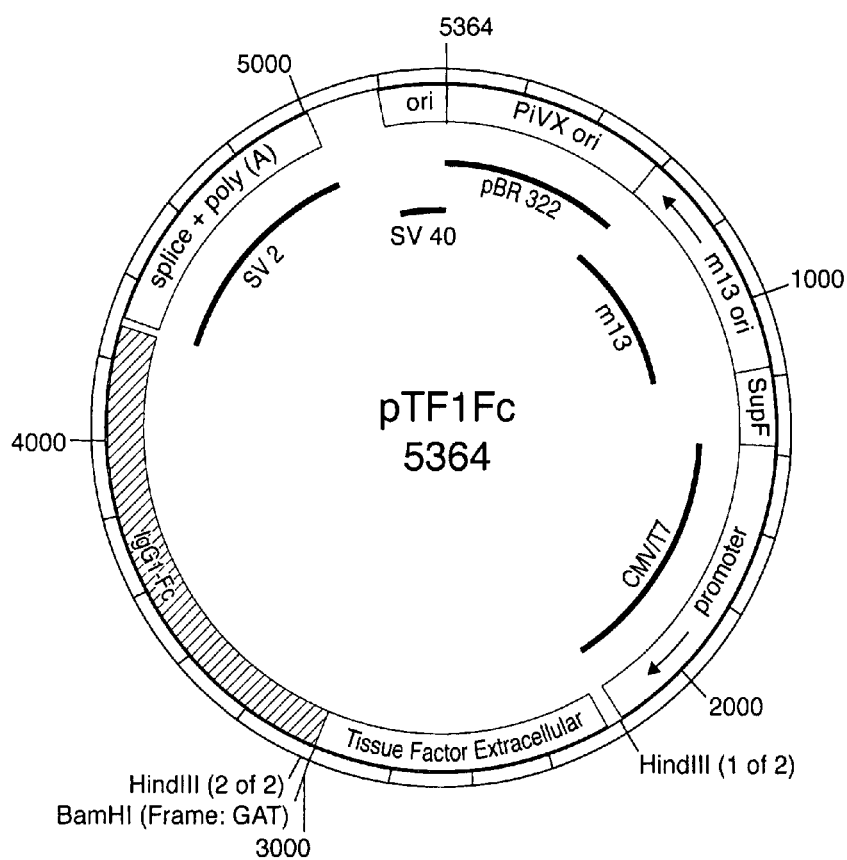
FIG. 4 depicts plasmid pTF1Fc.

Finally, the invention is explained in further examples.

EXAMPLE 1

Thromboplastin Fusion Proteins

Blood coagulation is a process of central importance in the human body. There is appropriately delicate regulation of the coagulation cascade, in which a large number of cellular factors and plasma proteins cooperate. These proteins (and their cofactors) in their entirety are called coagulation factors. The final products of the coagulation cascade are thrombin, which induces the aggregation of blood platelets, and fibrin which stabilizes the platelet thrombus. Thrombin catalyzes the formation of fibrin from fibrinogen and itself is formed by limited proteolysis of prothrombin. Activated factor X (factor Xa) is responsible for this step and, in the presence of factor Va and calcium ions, binds to platelet membranes and cleaves prothrombin.

Two ways exist for factor X to be activated, the extrinsic and the intrinsic pathway. In the intrinsic pathway a series of factors is activated by proteolysis in order for each of them to form active proteases. In the extrinsic pathway, there is increased synthesis of thromboplastin (tissue factor) by damaged cells, and it activates factor X, together with factor VIIa and calcium ions. It was formerly assumed that the activity of thromboplastin is confined to this reaction. However, the thromboplastin/VIIa complex also intervenes to activate the intrinsic pathway at the level of factor IX. Thus, a thromboplastin/VIIa complex is one of the most important physiological activators of blood coagulation.

It is therefore conceivable that thromboplastin, apart from its use as diagnostic aid (see below), can also be employed as constituent of therapeutic agents for treating inborn or acquired blood coagulation deficiencies. Examples of this are chronic hemophilias caused by a deficiency of factors VIII, IX or XI or else acute disturbances of blood coagulation as a consequence of, for example, liver or kidney disease. Use of such a therapeutic agent after surgical intervention would also be conceivable.

Thromboplastin is an integral membrane protein which does not belong to the immunoglobulin family. Thromboplastin cDNA sequences have been published by a total of four groups (Fisher et al., Thromb. Res., vol. 48 (1987), 89–99; Morrisey et al., Cell, vol. 50 (1987), 129–135; Scarpati et al., Biochemistry, vol. 26 (1987), 5234–5238; Spicer et al., Proc. Natl. Acad. Sci. USA, vol. 84 (1987), 5148–5152). Thromboplastin cDNA contains an open reading frame which codes for a polypeptide of 295 amino-acid residues, of which the 32 N-terminal amino acids set as signal peptide. Mature thromboplastin comprises 263 amino-acid residues and has a three-domain structure: i) amino-terminal extracellular domain (219 amino-acid residues); ii) transmembrane region (23 amino-acid residues); iii) cytoplasmic domain (carboxyl terminus; 21 amino-acid residues). In the extracellular domain there are three potential sites for N-glycosylation (Asn-X-Thr). Thromboplastin is normally glycosylated but glycosylation does not appear essential for the activity of the protein (Paborsky et al., Biochemistry, vol. 29 (1989), 8072–8077).

Thromboplastin is required as additive to plasma samples in diagnostic tests of coagulation. The coagulation status of the tested person can be found by the one-stage prothrombin clotting time determination (for example Quick's test). The thromboplastin required for diagnostic tests is currently obtained from human tissue, and the preparation process is difficult to standardize, the yield is low and considerable amounts of human starting material (placentae) must be supplied. On the other hand, it is to be expected that preparation of native, membrane-bound thromboplastin by genetic engineering will also be difficult owing to complex purification processes. These difficulties can be avoided by the fusion according to the invention to immunoglobulin portions.

The thromboplastin fusion proteins according to the invention are secreted by mammalian cells (for example CHO, BHK, COS cells) into the culture medium, purified by affinity chromatography on protein A-Sepharose and have surprisingly high activity in the one-stage prothrombin clotting time determination.

Cloning of Thromboplastin cDNA

The sequence published by Scarpati et al., Biochemistry, vol. 26 (1987), 5234–5238, was used for cloning the thromboplastin cDNA. Two oligonucleotide probe molecules (see FIG. 1) were derived from this. These two probe molecules were used to screen a cDNA bank from human placenta (Grundmann et al., Proc. Natl. Acad. Sci. USA, vol. 83 (1986), 8024–8028).

cDNA clones of various lengths were obtained. One clone, 2b-Apr5, which is used for the subsequent procedure, codes for the same amino-acid sequence as the cDNA described in Scarpati et al. FIG. 2 depicts the total sequence of the clone 2b-Apr5 with the thromboplastin amino-acid sequence deduced therefrom.

Construction of a Hybrid Plasmid pTF1Fc Coding for Thromboplastin Fusion Protein The plasmid pCD4E gamma 1 (EP 0 325 262 A2; deposited at the ATCC under the number No. 67610) is used for expression of a fusion protein composed of human CD4 receptor and human IgG1. The DNA sequence coding for the extracellular domain of CD4 is deleted from this plasmid using the restriction enzymes HindIII and BanHI. Only partial cleavage must be carried out with the enzyme HindIII in this case, in order to cut at only one of the two HindIII sites contained in pCD4E gamma 1 (position 2198). The result is an opened vector in which a eukaryotic transcription regulation sequence (promoter) is followed by the open HindIII site. The open BamHI site is located at the start of the coding regions for a pentapeptide linker, followed by the hinge and the CH2 and CH3 domains of human IgG1. The reading frame in the BamHI recognition sequence GGATCC is such that GAT is translated as aspartic acid. DNA amplification with thermostable DNA polymerase makes it possible to modify a given sequence in such a way that any desired sequences are attached at one or both ends. Two oligonucleotides able to hybridize with sequences in the 5'-untranslated region (A: 5' GATCGATTAAGCTTCG-GAACCCGCTCGATCTCGCCGCC 3') or coding region (B: 5' GCATATCTGGATCCCCGTA-GAATATTTCTCTGAATTCCCC 3') of thromboplastin cDNA were synthesized. Of these, oligonucleotide A is partially homologous with the sequence of the coding strand, and oligonucleotide B is partially homologous with the non-coding strand; cf. FIG. 3.

Thus, amplification results in a DNA fragment (827 bp) which contains (based on the coding strand) at the 5' end before the start of the coding sequence a HindIII site, and at the 3' end after the codon for the first three amino-acid residues of the transmembrane region a BamHI site. The reading frame in the BamHI cleavage site is such that ligation with the BamHI site in pCD4E gamma 1 results in a gene fusion with a reading frame continuous from the initiation codon of the thromboplastin cDNA to the stop codon of the heavy chain of IgG1. The desired fragment was obtained and, after treatment with HindIII and BamHI, ligated into the vector pCD4E gamma 1, as described above, which had been cut with HindIII (partially) and BamHI. The resulting plasmid was called pTF1Fc (FIG. 4).

Transfection of pTF1Fc Into Mammalian Cells

The fusion protein encoded by the plasmid pTF1Fc is called pTF1Fc hereinafter. pTF1Fc was transiently expressed in COS cells. For this purpose, COS cells were transfected with pTF1Fc with the aid of DEAE-dextran (EP A 0 325 262). Indirect immunofluorescence investigations revealed that the proportion of transfected cells was about 25%. 24 h after transfection, the cells were transferred into serum-free medium. This cell supernatant was harvested after a further three days.

Purification of pTF1Fc Fusion Protein from Cell Culture Supernatants 170 ml of supernatant from transiently transfected COS cells were collected overnight in a batch process in a column containing 0.8 ml of protein A-Sepharose at 4° C., washed with 10 volumes of washing buffer (50 mM tris buffer pH 8.6, 150 mM NaCl) and eluted in 0.5 ml fractions with eluting buffer (93:7 100 mM citric acid: 100 mM sodium citrate). The first 9 fractions were immediately neutralized with 0.1 ml of 2 M tris buffer pH 8.6 in each case and then combined, and the resulting protein was transferred by three concentration/dilution cycles in an Amicon microconcentrator (Centricon 30) into TNE buffer (50 mM tris buffer pH 7.4, 50 mM NaCl, 1 mM EDTA). The pTF1Fc obtained in this way is pure by SDS-PAGE electrophoresis (U. K. Lämmli, Nature 227 (1970) 680–685). In the absence of reducing agents it behaves in the SDS-PAGE like a dimer (about 165 KDa).

Biological Activity of Purified TF1Fc in the Prothrombin Clotting Time Determination TF1Fc fusion protein is active in low concentrations (>50 ng/ml) in the one-stage prothrombin clotting time determination (Vinazzer, H. Gerinnungsphysiologie und Methoden im Blutgerinnungslabor (1979), Fisher Verlag Stuttgart). The clotting times achieved are comparable with the clotting times obtained with thromboplastin isolated from human placenta.

EXAMPLE 2

Interleukin-4 Receptor Fusion Proteins

Interleukin-4 (IL-4) is synthesized by T cells and was originally called B-cell growth factor because it is able to stimulate B-cell proliferation. It exerts a large number of effects on these cells. One in particular is the stimulation of synthesis of molecules of immunoglobulin subclasses IgG1 and IgE in activated B cells (Coffmann et al., Immunol. Rev., vol. 102 (1988) 5). In addition, IL-4 also regulates the proliferation and differentiation of T cells and other hemopoietic cells. It thus contributes to the regulation of allergic and other immunological reactions. IL-4 binds with high affinity to a specific receptor. The cDNA which codes for the human IL-4 receptor has been isolated (Idzerda et al., J. Exp. Med., vol. 171 (1990) 861–873. It is evident from analysis of the amino-acid sequence deduced from the cDNA sequence that the IL-4 receptor is composed of a total of 825 amino acids, with the 25 N-terminal amino acids acting as signal peptide. Mature human IL-4 receptor is composed of 800 amino acids and, like thromboplastin, has a three-domain structure: i) amino-terminal extracellular domain (207 amino acids); ii) transmembrane region (24 amino acids) and iii) cytoplasmic domain (569 amino acids). In the extracellular domain there are six potential sites for N-glycosylation (Asn-X-Thr/Ser). IL-4 receptor has homologies with human Il-6 receptor, with the β-subunit of human IL-2 receptor, with mouse erythropoietin receptor and with rat prolactin receptor (Idzerda et al., loc. cit.). Thus, like thromboplastin, it is not a member of the immunoglobulin family but is assigned together with the homologous protein mentioned to the new family of hematopoietin receptors. Members of this family have four cysteine residues and a conserved sequence (Trp-Ser-X-Trp-Ser) in the extracellular domain located near the transmembrane region in common.

On the basis of the described function of the IL-4/IL-4 receptor system, there is a possible therapeutic use of a recombinant form of the IL-4 receptor for suppressing IL-4-mediated immune reactions (for example transplant rejection reaction, autoimmune diseases, allergic reactions).

The amount of substance required for therapy makes it necessary to prepare such molecules by genetic engineering. Because of the straightforward purification by affinity chromatography and improved pharmacokinetic properties, according to the invention the synthesis of soluble forms of the IL-4 receptor as immunoglobulin fusion protein is particularly advantageous.

The IL-4 receptor fusion proteins are secreted by mammalian cells (for example CHO, BHK, COS cells) into the culture medium, purified by affinity chromatography on protein A-Sepharose and have, surprisingly, identical functional properties to the extracellular domain of the intact membrane-bound IL-4 receptor molecule.

Figure 6:
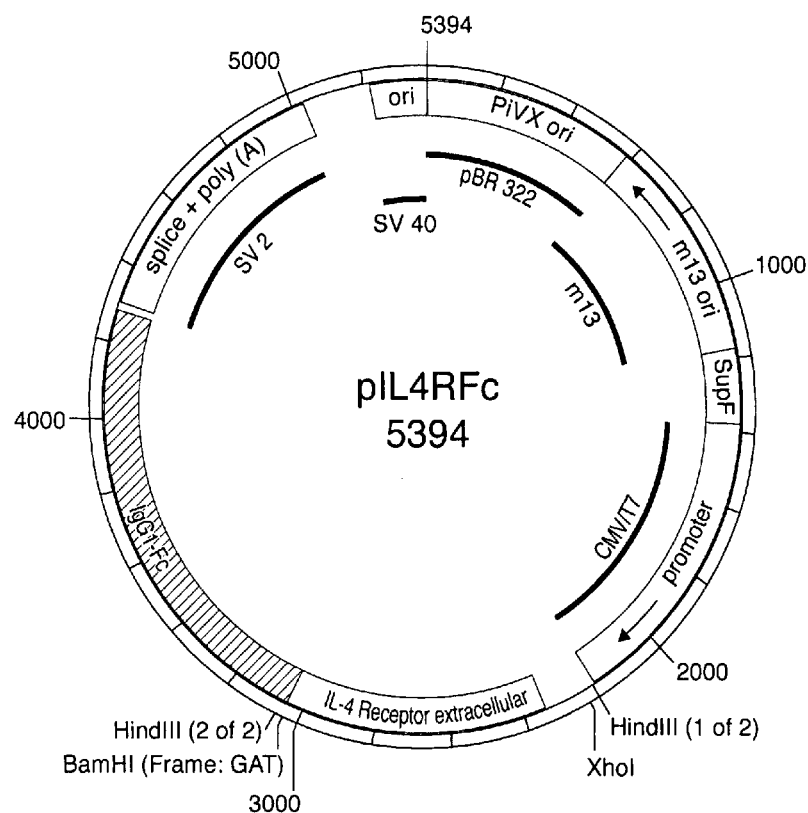
FIG. 6 depicts plasmid pIL4RFc.

Construction of a Hybrid Plasmid pIL-4RFc Coding for IL-4 Receptor Fusion Protein Cutting of the plasmid pCD4EGamma1 with XhoI and BamHI results in an opened vector in which the open XhoI site is located downstream from the promoter sequence. The open BamHI site is located at the start of the coding regions for a pentapeptide linker, followed by the hinge and the CH2 and CH3 domains of human IgG1. The reading frame in the BamHI recognition sequence GGATCC is such that GAT is translated as aspartic acid. DNA amplification with thermostable DNA polymerase makes it possible to modify a given sequence in such a way that any desired sequences can be attached at one or both ends. Two oligonucleotides able to hybridize with sequences in the 5'-untranslated region (A: 5' GATCCAGTACTCGAGAGAGAAGC-CGGGCGTGGTGGCTCATGC 3') or coding region (B: 5' CTATGACATGGATCCTGCTC-GAAGGGCTCCCTGTAGGAGTTGTG 3') of the IL-4 receptor cDNA which is cloned in the vector pDC302/T22-8 (Idzerda et al., loc. cit.) were synthesized. Of these, oligonucleotide A is partially homologous with the sequence of the coding strand, and oligonucleotide B is partially homologous with the non-coding strand; cf. FIG. 5. Amplification using thermostable DNA polymerase results in a DNA fragment (836 bp) which, based on the coding strand, contains at the 5' end before the start of the coding sequence an XhoI site, and at the 3' end before the last codon of the extracellular domain a BamHI site. The reading frame in the BamHI cleavage site is such that ligation with the BamHI site in pCD4E gamma 1 results in a gene fusion with a reading frame continuous from the initiation codon of the IL-4 receptor cDNA to the stop codon of the heavy chain of IgG1. The desired fragment was obtained and, after treatment with XhoI and BamHI, ligated into the vector pCD4E gamma 1, described above, which had been cut with XhoI/BamHI. The resulting plasmid was called pIL4RFc (FIG. 6).

Transfection of pIL4RFc into Mammalian Cells

The fusion protein encoded by the plasmid pIL4RFc is called pIL4RFc hereinafter. pIL4RFc was transiently expressed in COS cells. For this purpose, COS cells were transfected with pIL4RFc with the aid of DEAE-dextran (EP A 0 325 262). Indirect immunofluorescence investigations revealed that the proportion of transfected cells was about 25%. 24 h after transfection, the cells were transferred into serum-free medium. This cell supernatant was harvested after a further three day.

Purification of IL4RFc Fusion Protein From Cell Culture Supernatants 500 ml of supernatant from transiently transfected COS cells were collected overnight in a batch process in a column containing 1.6 ml of protein A-Sepharose at 4° C., washed with 10 volumes of washing buffer (50 mM tris buffer pH 8.6, 150 mM NaCl) and eluted in 0.5 ml fractions with eluting buffer (93:7 100 mM citric acid: 100 mM sodium citrate). The first 9 fractions were immediately neutralized with 0.1 ml of 2 M tris buffer pH 8.6 in each case and then combined, and the resulting protein was transferred by three concentration/dilution cycles in an Amicon microconcentrator (Centricon 30) into TNE buffer (50 mM tris buffer pH 7.4, 50 mM NaCl, 1 mM EDTA). The IL4RFc obtained in this way is pure by SDS-PAGE electrophoresis (U. K. Lämmli, Nature 227 (1970) 680–685). In the absence of reducing agents it behaves in the SDS-PAGE like a dimer (about 150 KDa).

Biological Activity of Purified IL4RFc

IL4RFc proteins binds $^{125}$I-radiolabeled IL-4 with the same affinity (Kd=0.5 nM) as membrane-bound intact IL-4 receptor. It inhibits the proliferation of IL-4-dependent cell line CTLLHuIL-4RI clone D (Idzerda et al., loc. cit.) in concentrations of 10–1000 ng/ml. In addition, it is outstandingly suitable for developing IL-4 binding assays because it can be bound via its Fc part to microtiter plates previously coated with, for example, rabbit anti-human IgG, and in this form likewise binds its ligands with high affinity.

EXAMPLE 3

Erythropoietin Fusion Proteins

Mature erythropoietin (EPO) is a glycoprotein which is composed of 166 amino acids and is essential for the development of erythrocytes. It stimulates the maturation and the terminal differentiation of erythroid precursor cells. The cDNA for human EPO has been cloned (EP-A-0 267 678) and codes for the 166 amino acids of mature EPO and a signal peptide of 22 amino acids which is essential for secretion. The cDNA can be used to prepare recombinant functional EPO in genetically manipulated mammalian cells and the EPO can be employed clinically for the therapy of anemic manifestations of various etiologies (for example associated with acute renal failure).

Because of the straightforward purification and the improved pharmacokinetic properties, according to the invention synthesis of EPO as immunoglobulin fusion protein is particularly advantageous.

Figure 8:
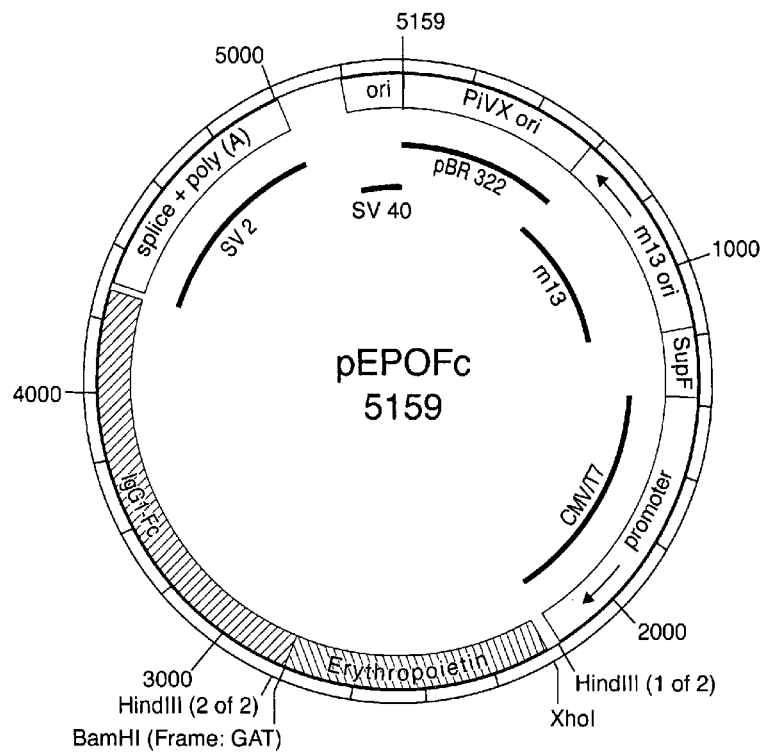
FIG. 8 depicts plasmid pEPOFc.

Construction of a Hybrid Plasmid pEPOFc Coding for Erythropoietin Fusion Protein This construction was carried out in analogy to that described in Example 2 (section: "Construction of a hybrid plasmid pIL-4RFc coding for IL-4 receptor fusion protein"). Two oligonucleotides able to hybridize with sequences in the vicinity of the initiation codon (A: 5'GATCGATCTC-GAGATGGGGGTGCACGAATGTCCTGC-CTGGCTGTGG 3') and of the stop codon (B: 5' CTG-GAATCGGATCCCCTGTCCTGCAGGCCTCCCCTGT GTACAGC 3') of the EPO cDNA cloned in the vector pCES (EP A 0 267 678) were synthesized. Of these, oligonucleotide A is partially homologous with the sequence of the coding strand, and oligonucleotide B is partially homologous with the non-coding strand; cf. FIG. 7. After amplification there is present with thermostable DNA polymerase a DNA fragment (598 bp) which, based on the coding strand, contains at the 5' end in front of the initiation codon an XhoI site and in which at the 3' end the codon for the penultimate C-terminal amino acid residue of the EPO (Asp) is present in a BamHI recognition sequence. The reading frame in the BamHI cleavage site is such that ligation with the BamHI site in pCD4E gamma 1 results in a gene fusion with a reading frame continuous from the initiation codon of EPO cDNA to the stop codon of the heavy chain of IgG1. The desired fragment was obtained and, after treatment with XhoI and BamHI, ligated into the vector pCD4E gamma 1, described above, which has been cut with XhoI/BamHI. The resulting plasmid was called pEPOFc (FIG. 8).

Accordingly, the present invention is inclusive of a process for preparing a fusion protein, which comprises:
(1) introducing DNA coding for these constructs into a mammalian cell expression system and,
(2) after expression, purifying the produced fusion protein by affinity chromatography via the immunoglobulin portion.

What is claimed is:
1. A soluble fusion protein comprising:
(1) a first amino acid sequence having the sequence of the amino-terminal extracellular domain of mature, human IL-4 receptor; and
(2) a second amino acid sequence having the sequence of the hinge, CH2, and CH3 domains of human IgG1, wherein said second amino acid sequence is linked to the carboxy terminal end of said first amino acid sequence.
2. A soluble fusion protein comprising the amino-terminal extracellular domain of mature, human IL-4 receptor linked to the hinge, CH2, and CH3 domains of human IgG1, wherein said fusion protein is encoded by a plasmid pIL4RFc.
3. The soluble fusion protein as claimed in claim 2, wherein said soluble fusion protein is expressed in a mammalian cell selected from the group consisting of CHO, BHK, and COS cells.
4. A dimer comprising two soluble fusion proteins as claimed in claim 1.
5. A dimer comprising two soluble fusion proteins as claimed in claim 2.
6. A dimer comprising two soluble fusion proteins as claimed in claim 3.

* * * * *

UNITED STATES PATENT AND TRADEMARK OFFICE
CERTIFICATE OF CORRECTION

| | | |
|---|---|---|
| PATENT NO. | : 7,253,264 B1 | Page 1 of 1 |
| APPLICATION NO. | : 08/293603 | |
| DATED | : August 7, 2007 | |
| INVENTOR(S) | : Lauffer et al. | |

It is certified that error appears in the above-identified patent and that said Letters Patent is hereby corrected as shown below:

On the Title Page, Item [75] under Inventors, replace "Marbury" with --Marburg--;

On the Title Page, Item [73] under Assignees, replace "Sanofi-Arentideutschland GmbH" with --Sanofi Aventis Deutschland GmbH--;

On the Title Page, Item [56] under References Cited, in Park et al., replace "11/1993" with --10/1993--.

Column 2, Line 13, replace "with thromboplastin amino acid sequence" with --with the thromboplastin amino acid sequence--.

Column 3,
    Line 16, replace "set" with --act--; and
    Line 17, replace "peptide" with --peptides--.

Column 4, Line 2, replace "BanHI" with --BamHI--.

Column 5,
    Line 44, replace "protein" with --proteins--; and
    Line 44, replace "hematopoietin" with --hematopoietic--.

Column 6, Line 48, replace "day" with --days--.

Column 8, Line 12, replace "has" with --had--.

Signed and Sealed this

Thirty-first Day of August, 2010

David J. Kappos
*Director of the United States Patent and Trademark Office*

UNITED STATES PATENT AND TRADEMARK OFFICE
CERTIFICATE OF CORRECTION

PATENT NO. : 7,253,264 B2
APPLICATION NO. : 08/293603
DATED : August 7, 2007
INVENTOR(S) : Lauffer et al.

It is certified that error appears in the above-identified patent and that said Letters Patent is hereby corrected as shown below:

Cover Sheet, Item (56) References Cited under U.S. PATENT DOCUMENTS, please add the following references:

--4,894,439   January 16, 1990      Dorin et al.--;
--5,055,447   October 8, 1991       Palladino et al.--;
--5,155,027   October 13, 1992      Sledziewski et al.--;
--5,447,851   September 5, 1995     Beutler et al.--.

Cover Sheet, under FOREIGN PATENT DOCUMENTS, please add the following references:

--EP  0418014  A1    March 20, 1991    EPO--.

Cover Sheet, under OTHER PUBLICATIONS, please add the following references:

--Ashkenazi et al., "Protection against Endotoxic Shock by a Tumor Necrosis Factor Receptor Immunoadhesin," Proc. Natl. Acad. Sci. U.S.A. 88:10535-10539 (1991).--;

--Engelmann et al., "A Tumor Necrosis Factor-Binding Protein Purified to Homogeneity from Human Urine Protects Cells from Tumor Necrosis Factor Toxicity," J. Biol. Chem. 264:11974-11980 (1989).--;

--Fernandez-Botran, "Soluble Cytokine Receptors: Their Role in Immunoregulation," FASEB J. 5:2567-2574 (1991).--;

--Fernandez-Botran and Vitetta, "A Soluble, High-Affinity, Interleukin-4-Binding Protein is Present in the Biological Fluids of Mice," Proc. Natl. Acad. Sci. U.S.A. 87:4202-4206 (1990).--;

Signed and Sealed this
Twenty-sixth Day of April, 2011

David J. Kappos
*Director of the United States Patent and Trademark Office*

--Fomsgaard et al., "Preliminary Study on Treatment of Septic Shock Patients with Antilipopolysaccharide IgG from Blood Donors," Scand. J. Infect. Dis. 21:697-708 (1989).--;

--Gray et al., "Cloning of Human Tumor Necrosis Factor (TNF) Receptor cDNA and Expression of Recombinant Soluble TNF-Binding Protein," Proc. Natl. Acad. Sci. U.S.A. 87:7380-7384 (1990).--;

--Himmler et al., "Molecular Cloning and Expression of Human and Rat Tumor Necrosis Factor Receptor Chain (p60) and Its Soluble Derivative, Tumor Necrosis Factor-binding Protein," DNA Cell Biol. 9:705-715 (1990).--;

--Idzerda et al., "Human Interleukin 4 Receptor Confers Biological Responsiveness and Defines a Novel Receptor Superfamily," J. Exp. Med. 171:861-873 (1990).--;

--Jacobs et al., "Pharmacokinetic Parameters and Biodistribution of Soluble Cytokine Receptors," Int. Rev. Exp. Pathol. 34B:123-135 (1993).--;

--Keegan et al., "Interleukin 4 Receptor: Signaling Mechanisms," Immunol. Today 15:423-432 (1994).--;

--Keegan and Pierce, "The Interleukin-4 Receptor: Signal Transduction by a Hematopoietin Receptor," J. Leukoc. Biol. 55:272-279 (1994).--;

--Kruse, "Conversion of Human Interleukin-4 into a High Affinity Antagonist by a Single Amino Acid Replacement," EMBO J. 11:3237-3244 (1992).--;

--Langner et al., "Structural and Functional Analysis of a TNF Receptor-Immunoglobulin Fusion Protein," in: New Advances on Cytokines, Romagnani et al., eds., New York: Raven Press pp. 349-354 (1992).--;

--Lesslauer et al., "Recombinant Soluble Tumor Necrosis Factor Receptor Proteins Protect Mice from Lipopolysaccharide-Induced Lethality," Eur. J. Immunol. 21:2883-2886 (1991).--;

--Liabakk et al., "A Rapid and Sensitive Immunoassay for Tumor Necrosis Factor Using Magnetic Monodisperse Polymer Particles," J. Immunol. Methods 134:253-259 (1990).--;

--Loetscher et al., "Molecular Cloning and Expression of the Human 55 kd Tumor Necrosis Factor Receptor," Cell 61:351-359 (1990).--;

--Loetscher et al., "Recombinant 55-kDa Tumor Necrosis Factor (TNF) Receptor: Stoichiometry of Binding to TNF alpha and TNF beta and Inhibition of TNF Activity," J. Biol. Chem. 266:18324-18329 (1991).--;

CERTIFICATE OF CORRECTION (continued)
U.S. Pat. No. 7,253,264 B2

--Maliszewski et al., "Cytokine Receptors and B Cell Functions: Recombinant Soluble Receptors Specifically Inhibit IL-1- and IL-4-Induced B Cell Activities In Vitro," J. Immunol. 144:3028-3033 (1990).--;

--Mosley et al., "The Murine Interleukin-4 Receptor: Molecular Cloning and Characterization of Secreted and Membrane Bound Forms," Cell 59:335-348 (1989).--;

--Novick et al., "Soluble Cytokine Receptors Are Present in Normal Human Urine," J. Exp. Med. 170:1409-1414 (1989).--;

--Novotny et al., "A Soluble, Single-Chain T-Cell Receptor Fragment Endowed with Antigen-Combining Properties," Proc. Natl. Acad. Sci. U.S.A. 88:8646-8650 (1991).--;

--Peppel et al., "A Tumor Necrosis Factor (TNF) Receptor-IgG Heavy Chain Chimeric Protein as a Bivalent Antagonist of TNF Activity," J. Exp. Med. 174:1483-1489 (1991).--;

--Redfield et al., "Secondary Structure and Topology of Human Interleukin 4 in Solution," Biochemistry 30:11029-11035 (1991).--;

--Schall et al., "Molecular Cloning and Expression of a Receptor for Human Tumor Necrosis Factor," Cell 61:361-370 (1990).--;

--Smith et al., "A Receptor for Tumor Necrosis Factor Defines an Unusual Family of Cellular and Viral Proteins," Science 248:1019-1023 (1990).--;

--Smith et al., "Multimeric Structure of the Tumor Necrosis Factor Receptor of HeLa Cells," J. Biol. Chem. 264:14646-14652 (1989).--;

--Traunecker et al., "Highly Efficient Neutralization of HIV with Recombinant CD4-Immunoglobulin Molecules," Nature 339:68-70 (1989).--;

--English Abstract for European Patent Document EP 0417563 A2, from Derwent World Patents Index, Dialog File 351.--.